(12) United States Patent
Palmér et al.

(10) Patent No.: US 6,252,113 B1
(45) Date of Patent: Jun. 26, 2001

(54) MANUFACTURING PROCESS OF METOPROLOL

(75) Inventors: Sven Palmér; Michael Sidenqvist, both of Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 08/973,144

(22) PCT Filed: Nov. 20, 1996

(86) PCT No.: PCT/SE97/01926

§ 371 Date: Nov. 26, 1997

§ 102(e) Date: Nov. 26, 1997

(87) PCT Pub. No.: WO98/22426

PCT Pub. Date: May 28, 1998

(30) Foreign Application Priority Data

Nov. 20, 1996 (SE) .................................................... 9604253

(51) Int. Cl.⁷ ........................ C07C 213/00; A01N 33/02
(52) U.S. Cl. ............................ 564/348; 514/652; 514/653
(58) Field of Search ................................ 564/348; 514/652, 514/653

(56) References Cited

FOREIGN PATENT DOCUMENTS

| 2011584 | 1/1990 | (ES) . |
| 9216197 | 10/1992 | (WO) . |

OTHER PUBLICATIONS

Chemical Abstracts, vol. 113, No. 21, Nov. 19, 1990, (Columbus, Ohio, USA), p. 677, The Abstract No. 190900r, ES, 2011584 A6, (Oranias Olsina, Gloria et al) Jan. 16, 1990.

Chemical Abstracts, vol. 119, No. 19, Aug. 11, 1993, (Columbus, Ohio, USA). Zjawiony, Jordan et al, p. 863, The Abstract No. 203128w, Pol. PL 158,497, 1992.

Zjawiony, et al., Chemical Abstracts 112: 658 (1990), Abstract No. 197820c.

*Primary Examiner*—Paul J. Killos
(74) *Attorney, Agent, or Firm*—White & Case LLP

(57) ABSTRACT

A method for the manufacture of metoprolol wherein the process is performed in water as solvent.

26 Claims, No Drawings

MANUFACTURING PROCESS OF METOPROLOL

FIELD OF THE INVENTION

The present invention relates to an improved method for the manufacture of metoprolol base 1-(isopropylamino)-3-[p-(2-methoxyethyl)-phenoxy]-2-propanol) via the route of reacting p-(2-methoxyethyl)-phenol (A) and epichlorohydrin (B) and then reacting the obtained 1-(2,3-epoxypropoxy)-4-(2-methoxyethyl)-benzene (AB) with isopropylamine (C). The crude metoprolol base is then purified.

Prior Art

Chemical Abstracts, vol. 112 (1990) abstract No. 197820 discloses the reaction of p-(2-methoxyethyl)-phenol and epichlorohydrin in the two phase system of water and organic solvent.

Swedish patents 354 851 and 368 004 disclose the reaction of p-(2-methoxyethyl)-phenol and epichlorohydrin where the epichlorohydrin is used not only as a building block in the reaction but also as solvent.

Disclosure of the Invention

It has now been found that metoprolol can be prepared in a manner that is fast, environmentally sound and gives a good yield and high purity using reactants that are known per se. The difference from the prior art is that the new method uses no other solvents than water for the reaction of A and B. From an environmental as well as an occupational hazard point of view it is a great advantage to be able to replace a hazardous organic solvent with a non-noxious solvent such as water.

The method of the invention is illustrated by the reaction scheme below:

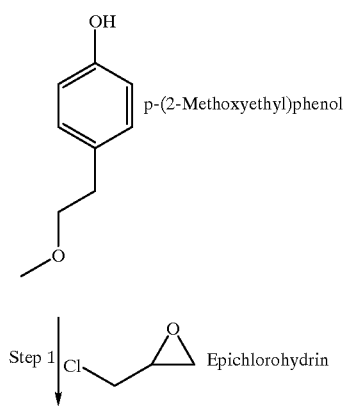

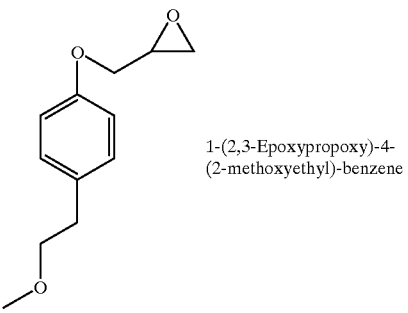

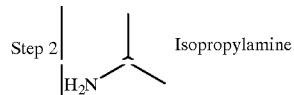

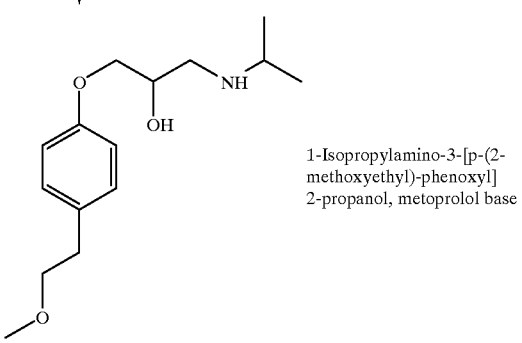

GENERAL EXAMPLE p-(2-Methoxyethyl)phenol (A) and epichlorohydrin (B, 1.4–2.0 eqv.) are reacted in water, at least 1.5 kg, preferably about 2 kg of water per kg of phenol, during the addition of sodium (or potassium) hydroxide solution, (1.3–1.7 eqv.) to form 1-(2,3-epoxypropoxy)-4-(2-methoxyethyl)benzene; (p-methoxyethyl-epoxypropoxybenzene). The reaction is preferably performed at a temperature of 50–70° C.

The two phases are separated, and the p-methoxyethylepoxy-propoxybenzene is isolated by distillation under reduced pressure. More particularly, the excess of epichlorohydrin is evaporated, and the epoxide is distilled under reduced pressure to obtain a product with a purity of about 96–98%. If desired, before distilling the main fraction of the epoxide, a prefraction/forecut (2–8%, preferably 4–6%) thereof could be distilled. The isolation by destillation of the epoxide under reduced pressure is an important part of the process and essential for the quality of the end product.

The epoxide is reacted with isopropylamine preferably in isopropyl alcohol to form metoprolol base. The amount of isopropylamine in relation to epoxide is at least 1 equivalent, preferably 3–6 equivalent. The reaction mixture is then treated in order to eliminate the excess of isopropylamine.

Alternatively, the amination with isopropylamine is carried out in a pressurized system without isopropyl alcohol at 70±10° C. at pressures of 2.8–3.2 kg/275–315 kPa.

The resulting metoprolol is dissolved in toluene, isobutyl methyl ketone or butyl acetate and extracted with dilute hydrochloric acid or sulphuric acid, preferably at pH 4–6. The phases are separated and the chosen solvent with sodium or potassium hydroxide solution to adjust the pH to 11–13 is added to the aqueous phase. The two phases are separated, and the organic phase is evaporated in vacuo to an oily residue of metoprolol base which is dissolved in acetone. Purified metoprolol base is then obtained by conventional means.

Working Example 1-(2,3-epoxypropoxy)-4-(2-methoxyethyl) benzene p-(2-Methoxyethyl)phenol (A, ~6.6 mol), epichlorohydrin (B, 1.45 eqv.) and water (~2 kg) were combined and the mixture heated to ~50° C.

Sodium hydroxide solution (50%; 1.4 eqv.) was added during 3 hours and the temperature was elevated to reach approximately 60° C. during the addition. Formation of the title compound occured during this period.

The batch was stirred for another hour at approximately 60° C., then cooled to approximately 50° C. and the phases were separated and the product washed with water.

The residue was distilled at $\leq 190°$ C. and a pressure of $\leq 20$ mm Hg and the distillate was collected. The yield of the title compound was 80% of theory and the purity was 98% according to GC analysis.

Metoprolol Base 1-(2,3-epoxypropoxy)-4-(2-methoxyethyl)benzene (1 kg, 4.8 mol), isopropyl alcohol (~0.9 kg) and isopropylamine (0.8–1.7 kg, 3–6 eqv.) were mixed and reacted for 2–5 hours at reflux. Formation of metoprolol base occurred during this period.

The reaction mixture was then concentrated at atmospheric pressure until the inner temperature reached ~100° C. Water was added to the batch and then distilled off in vacuo until the inner temperature reached ~100° C. to form a concentrate.

The resulting concentrate was diluted with isobutyl methyl ketone (~0.6 kg) and water (~2.2 kg), and concentrated sulphuric acid was added, to adjust the pH to 4–6.

After separation, isobutyl methyl ketone (~1 kg) was added to the water layer, and concentrated sodium hydroxide solution was added to adjust the pH to 13.

The organic layer was concentrated in vacuo at $\leq 80°$ C., until distillation ceased, and the concentrated batch was redissolved in acetone (~1.6 kg) and filtered, to yield metoprolol base solution. The assay of metoprolol base in the solution was determined by titration. Yield: ~1.2 kg metoprolol base (100%) ~95% of theory. The purity of the metoprolol base was 96%.

What is claimed is:

1. A method for the manufacture of metoprolol, which comprises reacting in a first step p-(2-methoxyethyl)phenol and epichlorohydrin in water as solvent and at a temperature of 50 to 70° C., evaporating the excess of epichlorohydrin and then distilling a prefraction/forecut of 2–8% before distilling the main fraction of the obtained 1-(2,3-epoxypropoxy)-4-(2-methoxyethyl)-benzene under reduced pressure, and in a second step reacting the obtained 1-(2,3-epoxypropoxy)-4-(2-methoxyethyl)-benzene and isopropylamine in the presence of isopropyl alcohol to form metoprolol base.

2. A method according to claim 1 wherein in the first step is carried out in the presence of sodium hydroxide.

3. A method according to claim 1 wherein in the first step is carried out in the presence of potassium hydroxide.

4. A method according to any of the preceding claims wherein the resulting metoprolol base is purified by dissolving the metoprolol base in a solvent selected among toluene, isobutyl methyl ketone and butyl acetate and extracted with either hydrochloric or sulphuric acid solution.

5. A method as claimed in any one of claims 1 to 3, wherein the resulting metoprolol is converted into metoprolol tartrate.

6. A method as claimed in any one of claims 1 to 3, wherein the resulting metoprolol is converted into metoprolol succinate.

7. A method for the manufacture of a pharmaceutical preparation, wherein metoprolol is produced by the method as claimed in any one of claims 1 to 3 and the metoprolol is thereafter formulated with a pharmaceutically acceptable diluent or carrier.

8. A method as claimed in claim 7 wherein a diuretic is included in the ingredients for the pharmaceutical preparation.

9. A method as claimed in claim 8 wherein the diuretic is hydrochlorothiazide.

10. A method as claimed in claim 4, wherein the resulting metoprolol is converted into metoprolol tartrate.

11. A method as claimed in claim 4, wherein the resulting metoprolol is converted into metoprolol succinate.

12. A method for the manufacture of a pharmaceutical preparation, wherein metoprolol is produced by the method as claimed in claim 4 and the metoprolol is thereafter formulated with a pharmaceutically acceptable diluent or carrier.

13. A method for the manufacture of a pharmaceutical preparation, wherein metoprolol is produced by the method as claimed in claim 6 and the metoprolol is thereafter formulated with a pharmaceutically acceptable diluent or carrier.

14. A method for the manufacture of a pharmaceutical preparation, wherein metoprolol is produced by the method as claimed in claim 7 and the metoprolol is thereafter formulated with a pharmaceutically acceptable diluent or carrier.

15. A method for the manufacture of a pharmaceutical preparation, wherein metoprolol is produced by the method as claimed in claim 11 and the metoprolol is thereafter formulated with a pharmaceutically acceptable diluent or carrier.

16. A method for the manufacture of a pharmaceutical preparation, wherein metoprolol is produced by the method as claimed in claim 11 and the metoprolol is thereafter formulated with a pharmaceutically acceptable diluent or carrier.

17. A method as claimed in claim 12 wherein a diuretic is included in the ingredients for the pharmaceutical preparation.

18. A method as claimed in claim 13 wherein a diuretic is included in the ingredients for the pharmaceutical preparation.

19. A method as claimed in claim 14 wherein a diuretic is included in the ingredients for the pharmaceutical preparation.

20. A method as claimed in claim 15 wherein a diuretic is included in the ingredients for the pharmaceutical preparation.

21. A method as claimed in claim 16 wherein a diuretic is included in the ingredients for the pharmaceutical preparation.

22. A method as claimed in claim 17 wherein the diuretic is hydrochlorothiazide.

23. A method as claimed in claim 18 wherein the diuretic is hydrochlorothiazide.

24. A method as claimed in claim 19 wherein the diuretic is hydrochlorothiazide.

25. A method as claimed in claim 20 wherein the diuretic is hydrochlorothiazide.

26. A method as claimed in claim 21 wherein the diuretic is hydrochlorothiazide.

* * * * *

UNITED STATES PATENT AND TRADEMARK OFFICE
CERTIFICATE OF CORRECTION

PATENT NO. : 6,252,113 B1
DATED : June 26, 2001
INVENTOR(S) : Palmér et al.

Page 1 of 1

It is certified that error appears in the above-identified patent and that said Letters Patent is hereby corrected as shown below:

<u>Column 4, claim 13,</u>
Line 31, "claim 6" should read -- claim 5 --.

<u>Column 4, claim 14,</u>
Line 36, "claim 7" should read -- claim 6 --.

<u>Column 4, claim 15,</u>
Line 41, "claim 11" should read -- claim 10 --.

Signed and Sealed this

First Day of January, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,252,113 B1
DATED : June 26, 2001
INVENTOR(S) : Palmér et al.

It is certified that error appears in the above-identified patent and that said Letters Patent is hereby corrected as shown below:

<u>Title page,</u>
Item [22], PCT Filing Date should read -- November 18, 1997 --.

Signed and Sealed this

Eleventh Day of June, 2002

Attest:

Attesting Officer

JAMES E. ROGAN
*Director of the United States Patent and Trademark Office*